US010959793B2

(12) United States Patent
Devengenzo et al.

(10) Patent No.: US 10,959,793 B2
(45) Date of Patent: Mar. 30, 2021

(54) MANIPULATOR ARM HAVING CONNECTION INTERFACE, AND RELATED DEVICES AND SYSTEMS

(71) Applicant: INTUITIVE SURGICAL OPERATIONS, INC., Sunnyvale, CA (US)

(72) Inventors: Roman L. Devengenzo, San Jose, CA (US); Alan W. Petersen, Cupertino, CA (US); Bruce M. Schena, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/558,845

(22) Filed: Sep. 3, 2019

(65) Prior Publication Data
US 2020/0060776 A1 Feb. 27, 2020

Related U.S. Application Data

(63) Continuation of application No. 15/126,734, filed as application No. PCT/US2015/020925 on Mar. 17, 2015, now Pat. No. 10,441,372.
(Continued)

(51) Int. Cl.
 A61B 34/35 (2016.01)
 A61B 34/30 (2016.01)
 (Continued)

(52) U.S. Cl.
 CPC .............. A61B 34/35 (2016.02); A61B 34/30 (2016.02); H01R 13/6582 (2013.01);
 (Continued)

(58) Field of Classification Search
 CPC ................................ H01R 33/00; A61B 34/74
 See application file for complete search history.

(56) References Cited

U.S. PATENT DOCUMENTS 3,366,918 A 1/1968 Johnson et al.
3,521,222 A 7/1970 Andrews et al.
(Continued)

FOREIGN PATENT DOCUMENTS

WO WO-2015127231 A1 8/2015

OTHER PUBLICATIONS

International Search Report and Written Opinion for Application No. PCT/US15/20925, dated Jun. 26, 2015, 12 pages.
(Continued)

Primary Examiner — Vicky A Johnson
(74) Attorney, Agent, or Firm — Jones Robb, PLLC

(57) ABSTRACT

A surgical instrument support arm of a teleoperated patient side cart may include a first arm portion including a first connector end and a second a second arm portion including a second connector end. The second arm portion may be removably connectable to the first arm portion via mating engagement of the first and second connector ends. The first and second connector ends may each include complementary mechanical connections and complementary electrical connections. At least one of the electrical connections of the first and second connector ends may include electrical shielding to protect against electrical interference in a position in which the electrical connections are matingly engaged. The electrical shielding may be configured to axially compress when the electrical connections of the first and second connector ends are matingly engaged.

22 Claims, 15 Drawing Sheets

Related U.S. Application Data

(60) Provisional application No. 61/954,195, filed on Mar. 17, 2014.

(51) Int. Cl.
   *H01R 13/6582* (2011.01)
   *H01R 33/00* (2006.01)
   *A61B 17/00* (2006.01)

(52) U.S. Cl.
   CPC .............. *H01R 33/00* (2013.01); *A61B 17/00* (2013.01); *A61B 2017/00477* (2013.01); *A61B 2034/301* (2016.02)

(56) References Cited

U.S. PATENT DOCUMENTS

| | | | |
|---|---|---|---|
| 3,609,632 A | 9/1971 | Vetter | |
| 3,678,445 A | 7/1972 | Brancaleone | |
| 3,835,443 A | 9/1974 | Arnold et al. | |
| 4,106,839 A | 8/1978 | Cooper | |
| 4,239,318 A | 12/1980 | Schwartz | |
| 4,243,290 A | 1/1981 | Williams | |
| 4,470,657 A | 9/1984 | Deacon | |
| 4,883,939 A | 11/1989 | Sagi | |
| 5,018,901 A | 5/1991 | Ferree et al. | |
| 5,139,890 A * | 8/1992 | Cowie | H01H 1/023 200/267 |
| 7,666,191 B2 | 2/2010 | Orban, III et al. | |
| 8,066,524 B2 * | 11/2011 | Burbank | C01B 3/36 439/247 |
| 8,545,515 B2 | 10/2013 | Prisco et al. | |
| 8,845,338 B2 | 9/2014 | Sirkett et al. | |
| 8,992,113 B2 | 3/2015 | Campagna et al. | |
| 9,586,327 B2 * | 3/2017 | Schena | B25J 19/0029 |
| 10,441,372 B2 * | 10/2019 | Devengenzo | A61B 34/35 |
| 2006/0175439 A1 | 8/2006 | Steur et al. | |
| 2007/0142970 A1 | 6/2007 | Burbank et al. | |
| 2007/0142971 A1 * | 6/2007 | Schena | A61B 34/30 700/251 |
| 2009/0280685 A1 * | 11/2009 | Gray | H01R 9/0527 439/607.41 |
| 2012/0124824 A1 | 5/2012 | Burbank et al. | |
| 2013/0325031 A1 | 12/2013 | Schena et al. | |
| 2013/0325033 A1 | 12/2013 | Schena et al. | |
| 2017/0095300 A1 | 4/2017 | Devengenzo et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

MANIPULATOR ARM HAVING CONNECTION INTERFACE, AND RELATED DEVICES AND SYSTEMS

CROSS-REFERENCE TO RELATED APPLICATIONS

This application is a continuation application of U.S. application Ser. No. 15/126,734, filed Sep. 26, 2016, which is a U.S. national stage application under 35 U.S.C. § 371(c) of International Application No. PCT/US2015/020925, filed Mar. 17, 2015, which claims the benefit of priority to U.S. Provisional Application No. 61/954,195, filed Mar. 17, 2014, each of which is incorporated by reference herein in their entirety.

TECHNICAL FIELD

Aspects of the present disclosure relate to manipulator arms of patient side carts for teleoperated surgical systems. More particularly, aspects of the present disclosure relate to connection interfaces for such manipulator arms.

BACKGROUND

Teleoperated surgical systems (sometimes referred to as "robotic surgical systems") may be used to perform minimally invasive medical procedures, with the surgical system actuating a surgical instrument according to commands provided by a user. Maintenance programs may be performed upon the surgical system, such as to repair, replace, or clean parts of the surgical system. To facilitate maintenance, one or more parts of the surgical system may be removable for repair, cleaning, or even replacement (temporary or otherwise). To minimize or eliminate downtime of the surgical system, it may be desirable to have those parts be field replaceable so the part can be removed in the field without having to take the entire system out of use. In the case of patient side cart manipulator arms of teleoperated surgical systems, there exists a continued need to improve upon the field replaceability of such parts, making replacement relatively easy by a user in the field and robust.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument support arm of a teleoperated patient side cart may comprise a first arm portion comprising a first connector end and a second a second arm portion comprising a second connector end. The second arm portion may be removably connectable to the first arm portion via mating engagement of the first and second connector ends. The first and second connector ends may each comprise complementary mechanical connections and complementary electrical connections. At least one of the electrical connections of the first and second connector ends may comprise electrical shielding to protect against electrical interference in a position in which the electrical connections are matingly engaged. The electrical shielding may be configured to axially compress when the electrical connections of the first and second connector ends are matingly engaged.

In accordance with at least one exemplary embodiment, a replaceable unit of surgical instrument support arm of a teleoperated patient side cart may comprise a proximal end and a distal end, and a connector interface located at one of the proximal end or the distal end. The connector interface may comprise a mechanical connection feature and an electrical connection feature. The electrical connection feature may comprise electrical shielding to protect against electrical interference in a position in which the electrical connection feature is matingly engaged with a complementary electrical connection feature. The electrical shielding may be configured to axially compress when the electrical connection feature and the complementary electrical connection feature are matingly engaged.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
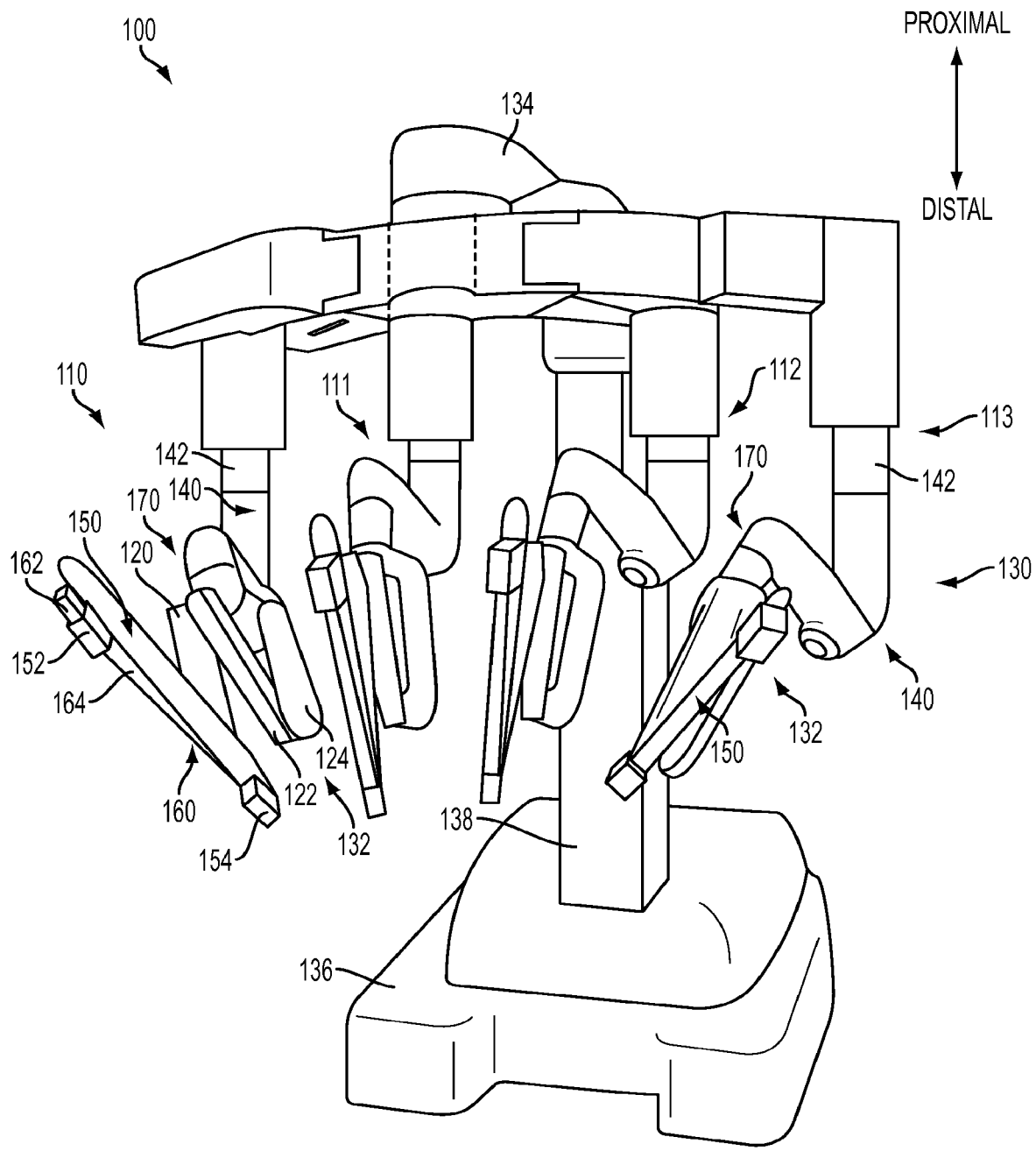
FIG. 1 is a perspective view of a patient side cart, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like.about.may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

It is desirable to provide a field replaceable portion of a manipulator arm and setup joint of a patient side cart to facilitate cleaning, repair, and replacement (temporary or otherwise) of the replaceable portion. The replaceable portion may include both mechanical and electrical connections in one unit, rather than in separate units, to facilitate removal and replacement of the replaceable portion. The resulting replaceable portion is easy to install and remove in the field and provides reliable and durable connections over a lifetime of the manipulator arm and setup joint.

Various exemplary embodiments of the present disclosure contemplate an arm of a patient side cart of a teleoperated surgical system including first and second arm portions and a connection interface including a mechanical connection and an electrical connection, with the electrical connection including a deformable electrical shielding member. Various exemplary embodiments further contemplate a patient side cart of a teleoperated surgical system including an arm with connectable and disconnectable first and second arm portions. According to various exemplary embodiments, the connection interface may be configured to permit connection and disconnection of the first and second arm portions from one another. The mechanical connections may be located on each of the first and second arm portions to join the first and second arm portions together. According to an exemplary embodiment, the mechanical connections comprise primary mechanical connections of the first and second arm portions that provide an initial mechanical connection when the first and second arm portions are initially connected. In an exemplary embodiment, the initial mechanical connection can include a pivotable connection permitting the first and second arm portions to swing relative to one another. According to an exemplary embodiment, the mechanical connections of the first and second arm portions further comprise secondary mechanical connections that engage when respective faces of connector ends are in planar contact. According to an exemplary embodiment, one of the first and second arm portions may comprise a protrusion and the other of the first and second arm portions comprise a recess configured to receive the protrusion when the first and second arm portions are connected. The protrusion and recess may facilitate alignment of the faces of the first and second arm portions when connecting the first and second arm portions.

According to various exemplary embodiments, each of the first and second arm portions may include electrical connections to form an electrical connection between the first and second arm portions. According to an exemplary embodiment, the electrical connections on the first and second arm portions comprise electrical shielding configured to axially compress when the first and second arm portions are connected to one another. The electrical shielding may be an electrical shielding member that includes gaps along an axial length of the shielding member, according to an exemplary embodiment. The electrical shielding member may be a spring, such as, for example, a wave spring. According to an exemplary embodiment, the electrical shielding member is made of a beryllium copper alloy. According to various exemplary embodiments, electrical connections of the first and second arm portions may comprise electrical pin arrays configured to engage one another when the first and second arm portions are connected to one another. The electrical shielding may surround the electrical connections, according to an exemplary embodiment.

Referring now to FIG. 1, an exemplary embodiment of a patient side cart 100 of a teleoperated surgical system is shown. A teleoperated surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Further, the exemplary embodiments described herein may be used, for example, with a da Vinci™ Surgical System available from Intuitive Surgical, Inc.

Patient side cart 100 may include a base 136, a main column 138, and a main boom 134 connected to main column 138. Patient side cart 100 may also include a plurality of arms 110, 111, 112, 113, which may each be connected to main boom 134. Portions of arms 110, 111, 112, 113 may be manipulated during a surgical procedure according to commands provided by a user at the surgeon console. In an exemplary embodiment, signal(s) or input(s) transmitted from a surgeon console may be transmitted to the control/vision cart, which may interpret the input(s) and generate command(s) or output(s) to be transmitted to the patient side cart 100 to cause manipulation of an instrument 160 (only one such instrument being mounted in FIG. 1) and/or portions of arm 110 to which the instrument 160 is coupled at the patient side cart 100.

Arms 110, 111, 112, 113 may each include an instrument mount portion 150 to which instrument 160 may be mounted. Instrument mount portion 150 may comprise an actuation interface assembly 152 and an accessory mount 154, with a shaft 164 of instrument 160 extending through accessory mount 154 (and on to a surgery site during a surgical procedure). A force transmission mechanism 162 of the instrument 160 connects with the actuation interface assembly 152. Accessory mount 154 may be configured to hold a cannula (not shown) through which shaft 164 of instrument 160 may extend to a surgery site during a surgical procedure. Actuation interface assembly 152 may contain a variety of drive and other mechanisms that are controlled to respond to input commands at the surgeon console and transmit forces to the force transmission mechanism 162 to actuate instrument 160, as those skilled in the art are familiar with.

Although the exemplary embodiment of FIG. 1 shows an instrument 160 attached to only arm 110 for ease of viewing, an instrument may be attached to any and each of arms 110, 111, 112, 113. An instrument 160 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. In the exemplary of FIG. 1, a surgical instrument with an end effector or an imaging instrument may be attached to and used with any of arms 110, 111, 112, 113. However, the embodiments described herein are not limited to the exemplary embodiment of FIG. 1 and various other teleoperated surgical system configurations may be used with the exemplary embodiments described herein.

An arm 110, 111, 112, 113 of patient side cart 100 may include portions that provide differing actuation capabilities. According to an exemplary embodiment, arm 110 includes a positioning portion and a driven portion. The positioning portion of arm 110 may be articulated to a desired position by a user but remains in a substantially fixed configuration during a surgical procedure. The positioning portion may be a referred to as a setup joint 130 and may form a proximal jointed portion of arm 110 that connects arm 110 to the main boom 134 of patient side cart 100, with proximal and distal directions labeled generally in the orientation of FIG. 1. Driven portion may be actively articulated during a surgical procedure according to the commands input by a user at the surgeon console. The driven portion may be referred to as a manipulator arm 132 and may form a distal portion of arm 110 from setup joint 130 to instrument mount portion 150. Manipulator arm 132 may include members that can be actively articulated relative to one another to orient and position various parts of manipulator arm 132. As shown in the exemplary embodiment of FIG. 1, manipulator arm 132 may include links 120, 122, 124 that can be moved relative to one another. Although manipulator arm 132 is shown as including links 120, 122, 124 in the exemplary embodiment of FIG. 1, the manipulator arms of the exemplary embodiments described herein are not limited to three links and may include fewer links or a greater number of links, such as, for example, one link, two links, four links, five links, six links, and so on.

Although the exemplary embodiments described herein may reference setup joint 130 and manipulator arm 132 with regard to arm 110, arms 111, 112, 113 may each include a setup joint 130 and manipulator arm 132 according to the embodiments shown and described herein.

Maintenance programs may be performed upon a patient side cart 100, such as to repair, replace, or clean all or part(s) of an arm 110, 111, 112, 113. To facilitate efficient use of patient side cart 100, a portion of the cart may be field replaceable so that the entire cart 100 need not be taken out of service. For instance, a portion of an arm 110, 111, 112, 113 may be removable so the removed portion may be repaired, cleaned, or even replaced (temporarily or permanently) with a replacement portion that is installed to permit the arm and patient side cart 100 to remain active, thus minimizing or eliminating down time of a surgical system using the patient side cart 100.

Figure 2:
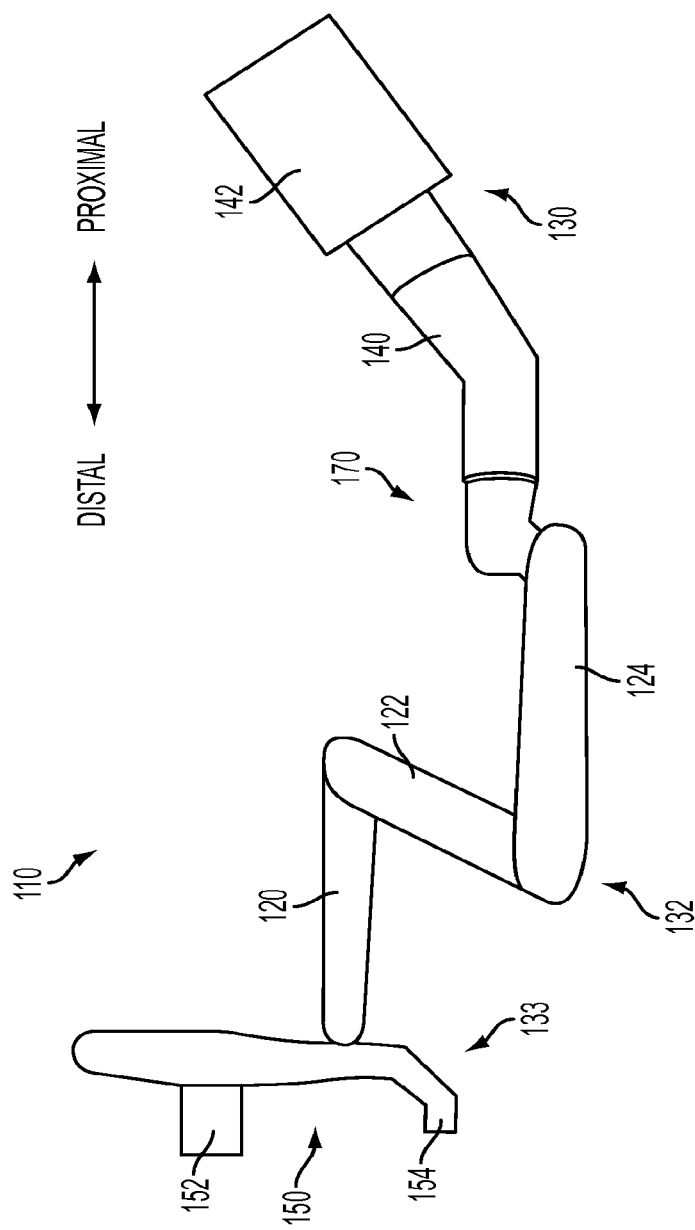
FIG. 2 is a side view of a manipulator arm and setup joint of the patient side cart of FIG. 1 with the manipulator arm in a partially extended configuration.

Turning to FIG. 2, a side view of arm 110 of patient side cart 100 of FIG. 1 is illustrated, with arm 110 in a partially extended configuration. A distal portion 133 of manipulator arm 132 may include the instrument mount portion 150 comprising an actuation interface assembly 152 and an accessory mount 154, as discussed above with regard to the exemplary embodiment of FIG. 1. A proximal portion 135 of manipulator arm 132 may be connected to setup joint 130 of arm 110, such as a distal setup section 140 of setup joint 130. Setup joint 130 may further include a proximal setup section 142 that the distal setup section 140 is connected to, as shown in the exemplary embodiment of FIG. 2. Distal setup section 140 and proximal setup section 142 also are shown for arm 113 in FIG. 1, for ease of viewing. Proximal section 142 of setup joint 130 may in turn be connected to a main body of patient side cart 100, such as main boom 134 in the exemplary embodiment of FIG. 1.

Figure 3:
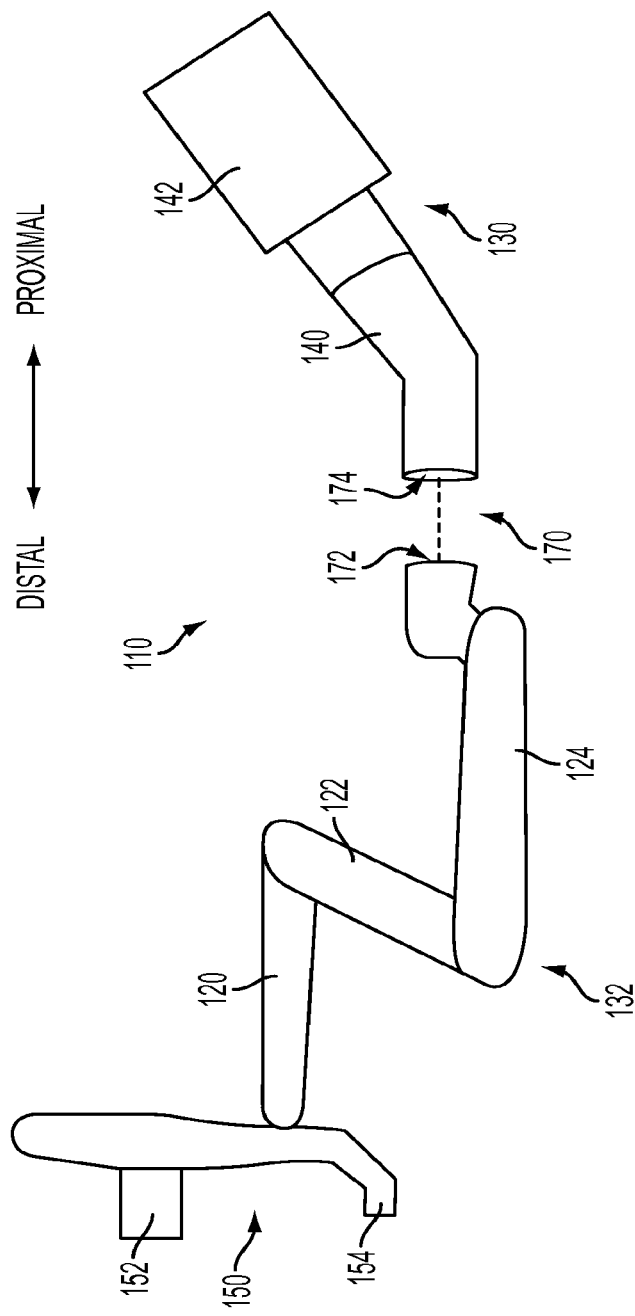
FIG. 3 shows the manipulator arm and setup joint of FIG. 2 in a disconnected state.

According to an exemplary embodiment, arm 110 may include a connection interface 170 between manipulator arm 132 and setup joint 130 to connect manipulator arm 132 and setup joint 130. Thus, manipulator arm 132 may be a removable portion of arm 110 that can be disconnected from setup joint 130, permitting manipulator arm 132 to be cleaned, repaired, or replaced, with setup joint 130 remaining attached to patient side cart 100. Turning to FIG. 3, the manipulator arm 132 and setup portion 130 are shown in a disconnected state. As shown in the exemplary embodiment of FIG. 3, connection interface 170 of arm may comprise a proximal connector end 172 of manipulator arm 132 and a distal connector end 174 of setup joint 130, with the proximal connector end 172 of manipulator arm 132 and the distal connector end 174 of setup joint 130 connecting to one another, as shown in the exemplary embodiment of FIG. 2. The distal connector end 174 of setup joint 130 may be, for example, the distal end of distal setup section 140, as shown in the exemplary embodiment of FIG. 3. For ease of viewing, connection interface 170 also is shown between manipulator arm 132 and setup joint 130 in the exemplary embodiment of FIG.

Figure 4:
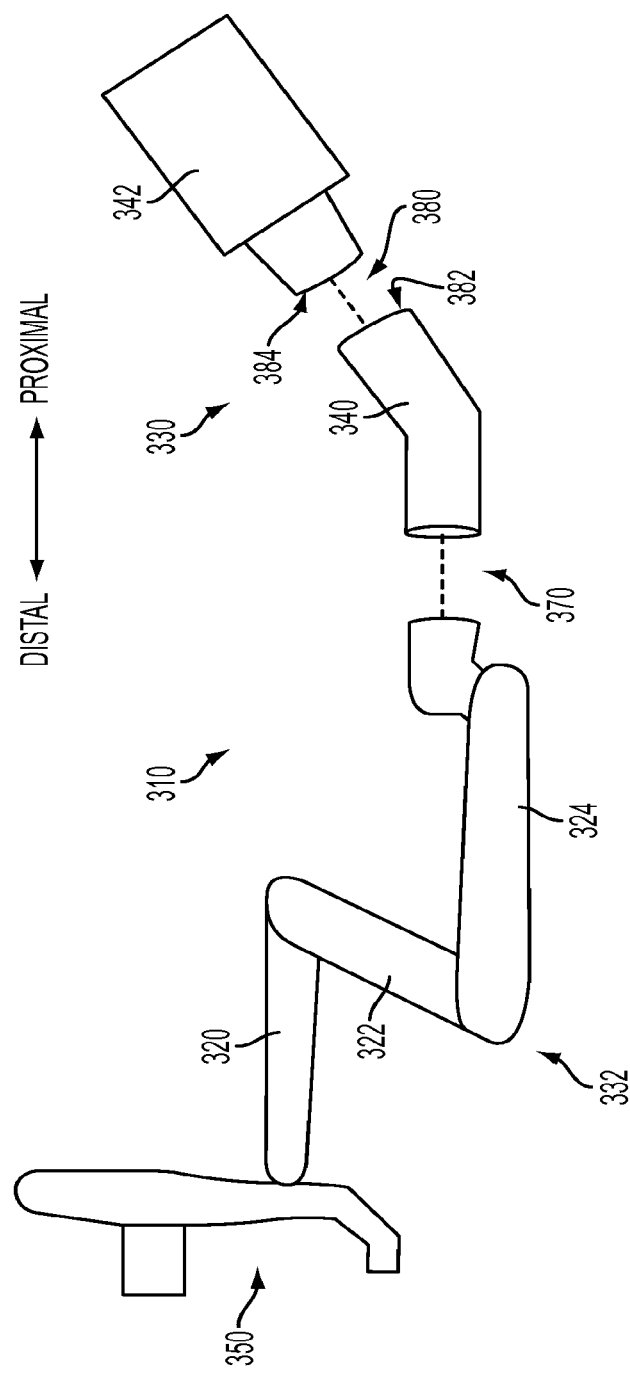
FIG. 4 shows a side view of an exemplary embodiment of a patient side cart manipulator arm disconnected from a setup joint, and with the setup joint further disconnected into sections.

A connection interface may be located elsewhere in an arm of a patient side cart than between a manipulator arm and setup joint of the arm. For example, one or more connection interfaces may be located within the setup joint to permit different sections of the setup joint to be relatively easily disconnected from and connected to one another, such as to clean, repair, or replace a section of the setup joint. Providing one or more connection interfaces within the setup joint may permit the setup joint to be separated into multiple pieces, which would be lighter and easier to handle than the entire setup joint. Turning to FIG. 4, a side view of an arm 310 is shown, such as for the patient side cart 100 of the exemplary embodiment of FIG. 1, which includes a manipulator arm 332 and a setup joint 330. Manipulator arm 332 may comprise one or more links, such as, for example, links 320, 322, 324 and an instrument mount portion 350, as described above in regard to the exemplary embodiments of FIGS. 1 and 2.

According to an exemplary embodiment, arm 310 includes two connection interfaces 370, 380 (shown separated). Connection interface 370 provides a connection between a manipulator arm 332 and setup section 330, as described above with respect to FIGS. 2 and 3. Setup joint 330 also may include a connection interface 380 to permit one or more sections of setup joint 330 to be disconnected, such as for cleaning, repair, or replacement. As shown in the exemplary embodiment of FIG. 4, connection interface 380 may be located between a distal setup section 340 and a proximal setup section 342. For instance, a proximal connector end 382 of distal setup section 340 may be configured to connect with a distal connector end 384. Thus, distal setup section 340 may be a replaceable portion of arm 310 that can be removed and replaced with another distal setup section 340 of the same configuration.

In another example, one or more connection interfaces may be located within the manipulator arm. For instance, connection interface(s) may be located between one or more pairs of links 120, 122, 124 of manipulator arm 132 so that one or more links 120, 122, 124 may be disconnected for cleaning, repair, or replacement. In view of this, the exemplary embodiments of connection interfaces described herein may be applied not only to a connection interface between a manipulator arm and a setup portion, but to connection interfaces located within a setup joint and connection interfaces located within a manipulator arm. Further, the exemplary embodiments of connection interfaces described herein may be applied not only to arms of a patient side cart of a teleoperated surgical system but also to other connection interfaces between parts that may be disconnected, such as for cleaning, repair, or replacement.

Figure 5:
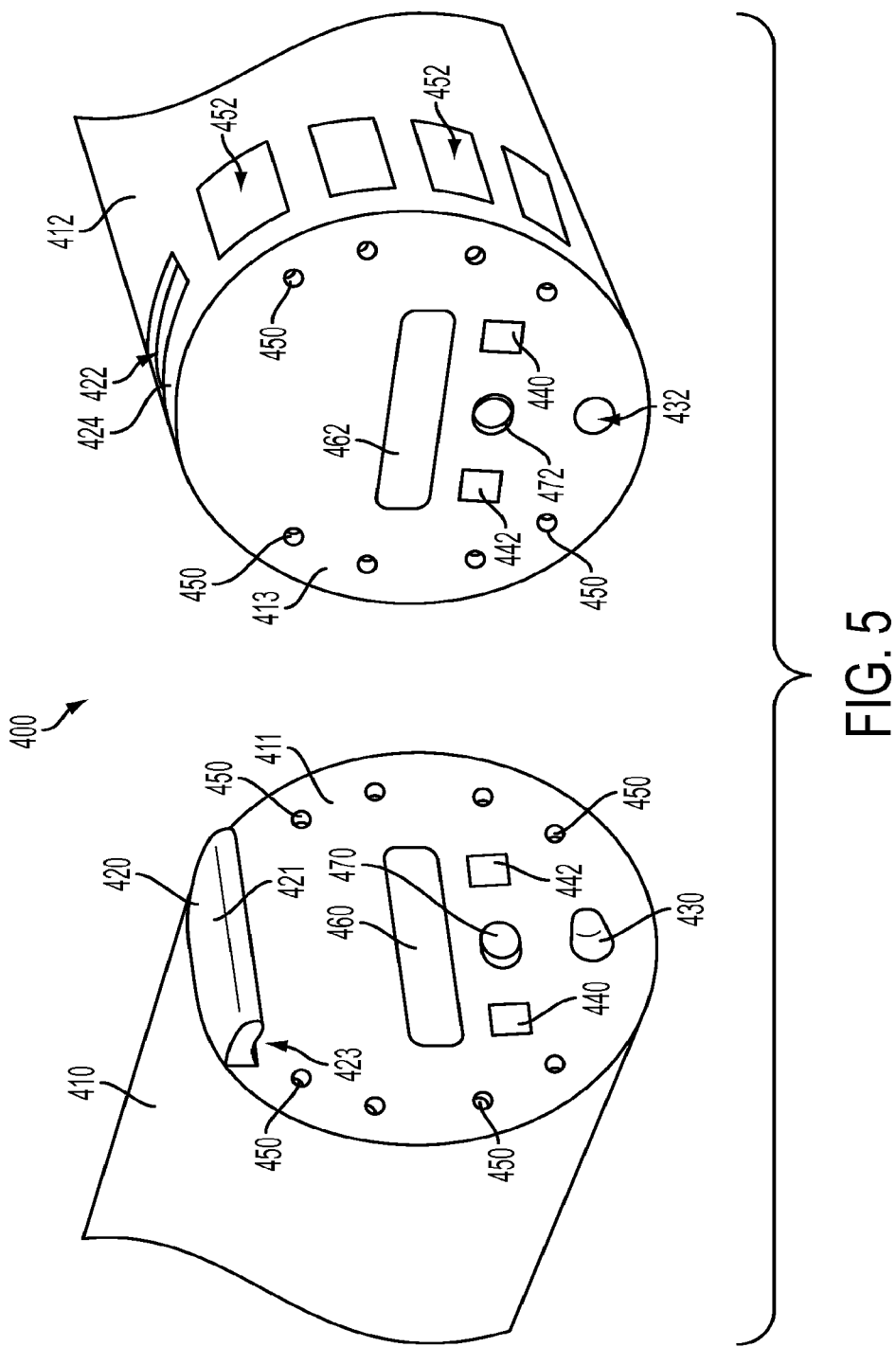
FIG. 5 shows a perspective end view of a connection interface between connector ends, according to an exemplary embodiment.

A connection interface in accordance with various exemplary embodiments may comprise a mechanical connection with structures that physically connect two connector ends of differing parts together. Turning to FIG. 5, an exemplary embodiment is shown of a connection interface 400 between a first connector end 410 and a second connector end 412 of two components, with connector ends 410 and 412 in a disconnected state. Connector ends 410 and 412 may be a proximal end 172 of a manipulator arm 132 and a distal connector end 174 of a setup joint 130, as discussed above with regard to the exemplary embodiment of FIG. 3, or may be a proximal connector end 382 of a distal setup section 340 and a distal connector end 384 of a proximal setup section 342, as discussed above with regard to the exemplary embodiment of FIG. 4. In other exemplary embodiments, the connector ends 410, 412 may be other connector ends located between sections within a manipulator arm or between various other components.

Connector ends 410 and 412 may include multiple mechanical connection structures to mechanically engage connector ends 410 and 412 together. Such connector structures may include one or more primary mechanical connections that provides an initial mechanical connection between connector ends 410 and 412. As shown in the exemplary embodiment of FIG. 5, connector end 410 may include a hook 420, or other latch structure, and connector end 412 may include a slot 422 to receive hook 420, or other latch structure. Those skilled in the art would appreciate that the locations of hook 420, or other latch structure, and slot 422 may be reversed on connector ends 410 and 412. A tip 421 of hook 420 may be inserted into slot 422 to form a primary mechanical connection when connector ends 410 and 412 (and thus the parts with which those connector end faces are associated with, such as, for example, a manipulator arm 132, 332 and setup joint 130, 330) are initially connected. Connector end 412 may further include a ridge 424 that hook 420 is seated upon, such as by seating concave portion 423 of hook 420 onto ridge 424 when hook 420 is inserted into slot 422, according to an exemplary embodiment. Concave portion 423 of hook 420 and ridge 424 may have corresponding surface shapes to facilitate seating concave portion 423 and ridge 424 to one another.

Connector ends 410 and 412 also may include one or more secondary mechanical connections to provide full mechanical engagement to connection interface 400. For example, connector ends 410 and 412 may include one or more latches 440, 442 (shown schematically in the exemplary embodiment of FIG. 5) that fasten to one another when the respective faces 411 and 413 of connector ends 410 and 412 are fully engaged one another, such as in a mating, planar engagement of face 411 of connector end 410 with face 413 of connector end 412. Latches 440, 442 may be positive engaging latches, such as, for example, spring latches, torsion spring latches, magnets, or other types of latches one of ordinary skill in the art is familiar with. Secondary mechanical connections between connector ends 410 and 412 include fasteners to connect connector ends 410 and 412, such as, for example, screws, bolts, or other types of fasteners inserted through holes 450 in connector ends 410 and 412. According to an exemplary embodiment, one or both of connector ends 410 and 412 may include apertures for inserting a fastener and accessing the fastener with a tool, such as, for example, a screwdriver. In the exemplary embodiment of FIG. 5, exemplary apertures 452 are depicted on connector end 412.

Aside from structures to mechanically connect connector ends 410 and 412, connection interface 400 may include one or more guide structures to align faces 411 and 413 (as well as complementary connection structures of faces 411 and 413) when the connector ends 410 and 412 are brought together. According to an exemplary embodiment, connector end 410 may include a protrusion 430 and connector end 412 may include a recess 432 configured (e.g., sized and shaped) to receive protrusion 430, although the locations of protrusion 430 and recess 432 may be reversed upon connector ends 410 and 412. Protrusion 430 inserts into recess 432 to align faces 411 and 413 with one another.

Figure 6:
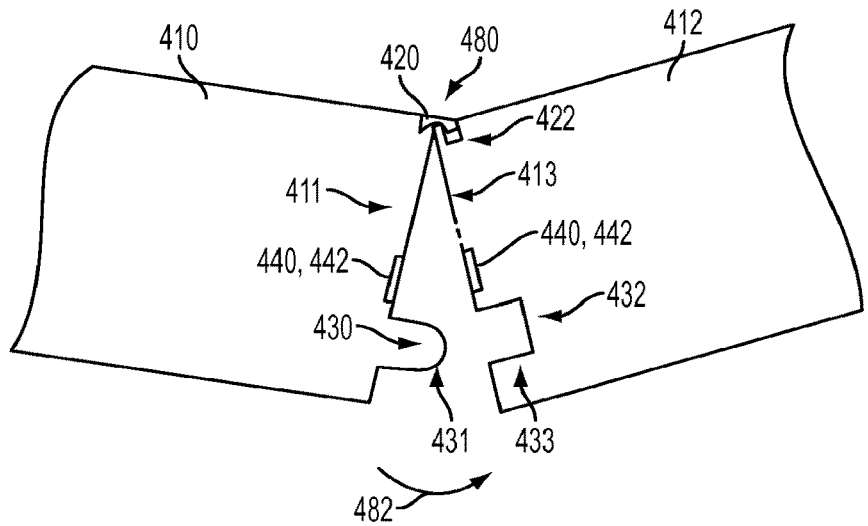
FIG. 6 shows a side view of an initial primary mechanical connection between the connector ends of FIG. 5, according to an exemplary embodiment.
Figure 7:
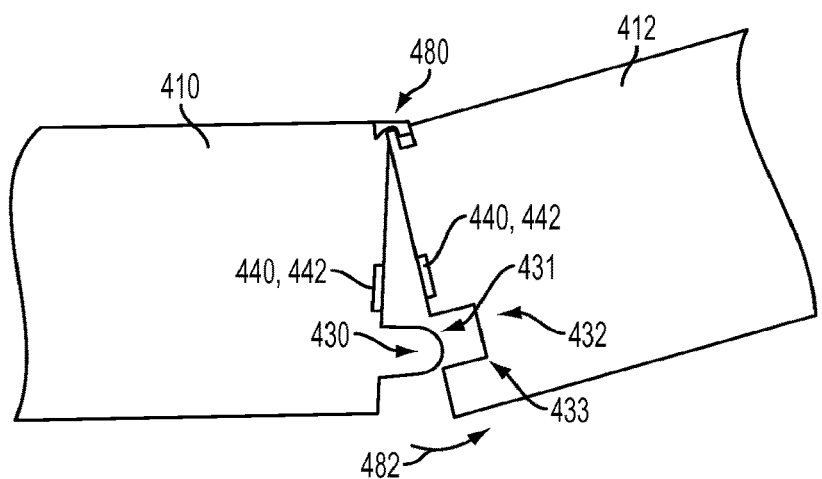
FIG. 7 shows the two connector ends of FIG. 6 after one has swung towards the other.
Figure 8:
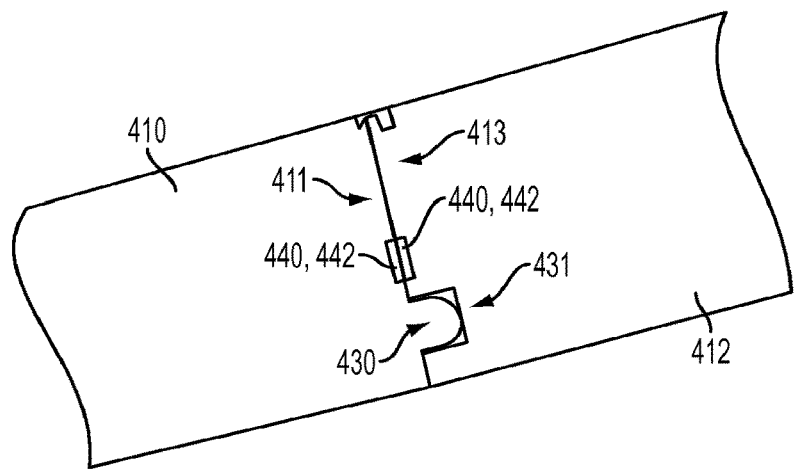
FIG. 8 shows the two connector ends of FIGS. 6 and 7 in a fully connected state.

As discussed above, a connection interface may include a primary mechanical connection that forms an initial connection as connector ends are initially brought together, and secondary mechanical connections that fully engage the connector ends when faces of the connector ends are brought in planar, mating engagement with one another. The secondary mechanical connection may also provide structural rigidity between connector ends as well, in addition to structural rigidity provided by other structures, such as, for example, a primary mechanical connection. Turning to FIGS. 6-8, an exemplary embodiment depicting mechanical connection aspects of connector ends 410 and 412 are shown. Other features of the connector ends 410, 412 are not shown for simplicity. In FIG. 6, connector ends 410 and 412 have been initially connected to one another by a primary mechanical connection. As described above, the primary mechanical connection may be, for example, hook 420 fixed to connector end 410, which is inserted into a recess 422 of connector end 412, as discussed above in regard to the exemplary embodiment of FIG. 5.

According to an exemplary embodiment, primary mechanical connection 487 forms a pivot point about which connector ends 410, 412 may swing relative to each other. For instance, if connector end 412 is an end of a setup joint, such as setup joint 130 of the exemplary embodiment of FIG. 1, and connector end 410 is an end of a manipulator arm, such as manipulator arm 132 of the exemplary embodiment of FIG. 1, connector end 412 may be substantially fixed (e.g., to the remainder of the setup portion and patient side cart) while connector end 410 is free to swing about the pivot axis 480 of the primary mechanical connection toward connector end 412 to bring face 411 of connector end 410 toward face 413 of connector end 412, with the swing along direction 482 indicated in FIG. 6. Further, if connector end 412 is an end of a proximal setup section, such as proximal setup section 142 of the exemplary embodiment of FIG. 1, and connector end 410 is an end of a distal setup section, such as distal setup section 142 of the exemplary embodiment of FIG. 1, connector end 412 may be fixed while connector end 410 is free to swing.

Movement of connector end 410 relative to connector end 412 may continue until faces 411 and 413 come into planar contact, as shown in the exemplary embodiment of FIG. 8, to complete the connection of connector ends 410 and 412. Connector ends 410 and 412 may include additional secondary mechanical connections 440, 442, as discussed above with regard to the exemplary embodiment of FIG. 5, which engage and join connector ends 480 and 490 when faces 411 and 413 come into contact, as shown in FIG. 8.

A tip 431 of protrusion 430 may have a rounded shape, such as, for example, a dome or bullet shape, as shown in the exemplary embodiment of FIGS. 6-8. Because of its rounded shape or other tapered shape, tip 431, which is the initial part of protrusion 430 inserted into recess 432, is smaller than the remainder of protrusion 430. As a result, if faces 411 and 413 are misaligned and protrusion 430 is off-center of recess 432 as connector end 410 is swung toward connector end 412 along direction 482, tip 431 may still be inserted into recess 432. If the faces 411 and 413 are misaligned, tip 431 or the protrusion 430 itself may contact a sidewall 433 of recess 432 (or edge of recess 432), which in turn can force protrusion 430 toward a center of recess 432 as the protrusion 430 is inserted. This insertion and centering of the protrusion 430 within the recess in turn aligns faces 411 and 413 as protrusion 430 is inserted further into recess 432.

A connection interface may comprise other connections in addition to or independently of a mechanical connection. For example, the connection interface 400 of the exemplary embodiment of FIG. 5 may include one or more electrical connections, such as electrical connections 460 and 470 in connector end 410 and electrical connections 462 and 472 in connector end 412, with connections 460 and 462 and connections 470 and 472 respectively mating with one another when faces 411 and 413 of connector ends 410 and 412 are in planar contact with one another. Electrical connections 460, 462, 470, and 472 are shown schematically in FIG. 5 and may include various types of electrical connections for transmitting electrical power and/or signals (e.g., data signals, control signals, or other types of signals) across electrical connections 460, 462, 470, and 472 when electrical connections 460 and 462 are mated with one another.

Figure 10:
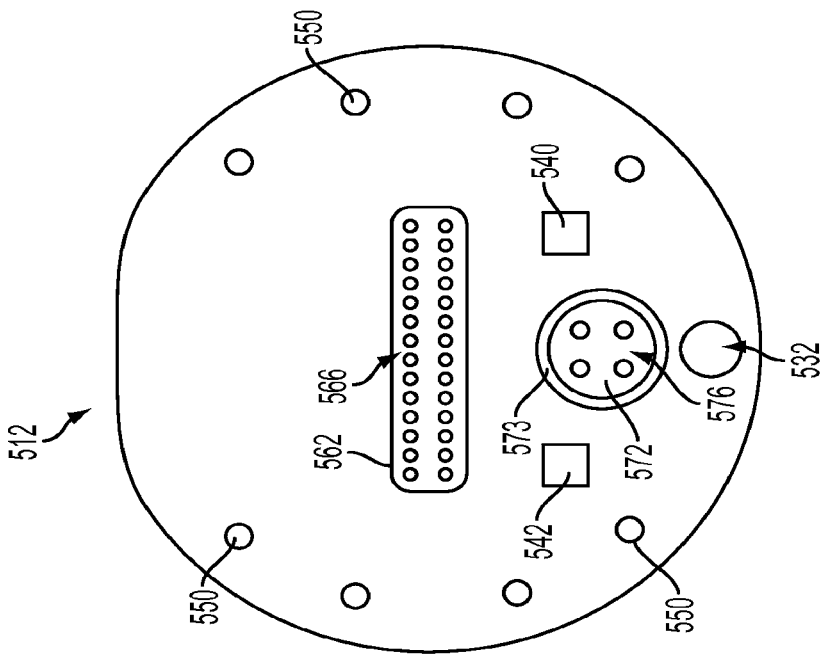
FIG. 10 shows an end view of a connector end including mechanical and electrical connections, according to an exemplary embodiment.
Figure 9:
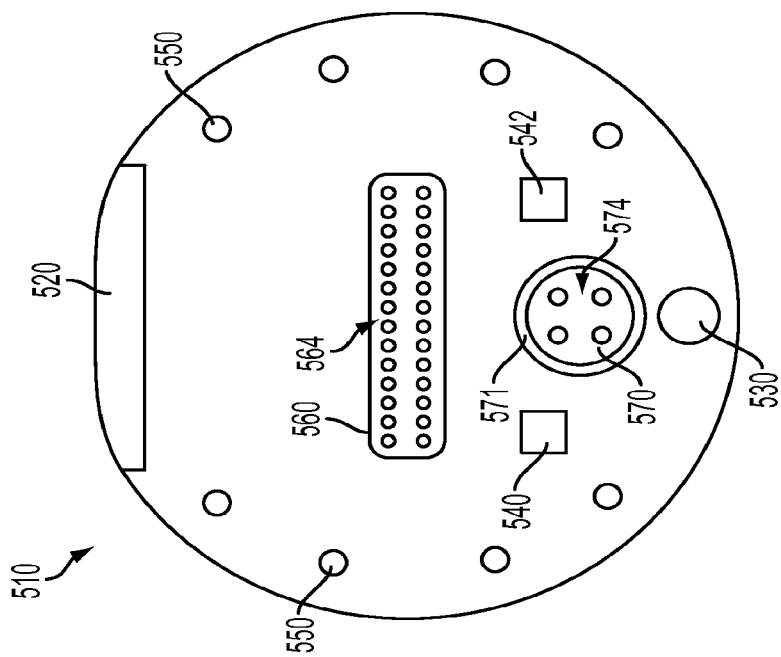
FIG. 9 shows an end view of an end of a connector end including mechanical and electrical connections, according to an exemplary embodiment.

Turning to FIGS. 9 and 10, end views of a first connector end 510 and a second connector end 512 are respectively shown. Connects ends 510, 512 may be function as described above with regard to the embodiments of FIGS. 5-8. For instance, first connector end 510 may include a hook 520, a protrusion 530, latches 540 and 542, and holes 550 for fasteners, and second connector end 512 may include recess 532, latches 540 and 542, and holes 550 for fasteners, as described above with regard to the exemplary embodiment of FIG. 5. Further, connector ends 510 and 512 may respectively include first electrical connections 560 and 562. First electrical connections 560 and 562 may be used to transmit electrical energy and provide an electrical ground when connector ends 510 and 512 are mated with one another, such as according to the exemplary embodiment of FIGS. 6-8, to form an electrical connection between connections 560 and 562.

To transmit electrical energy, electrical connections 560 and 562 may include one or more electrical connectors that engage with one another when electrical connections 560 and 562 are joined. Electrical connections 560 and 562 may further include a ground, according to an exemplary embodiment. Electrical connectors may include, for example, pins or other types of electrical connectors one of ordinary skill in the art is familiar with. According to an exemplary embodiment, electrical connections 560 and 562 may respectively include arrays of pins 564 and 566 that engage one another to form an electrical connection when electrical connections 560 and 562 are engaged. Pin arrays 564 and 566 may each include a number of pins according to a desired use of the pins, such as, for example, according to how much power is transmitted via pin arrays 564 and 566. According to an exemplary embodiment, pins arrays 564 and 566 may each include, for example, 28 pins, such as for a 12V, 48V electrical connection, although other numbers of pins in arrays 564 and 566 may be utilized.

Figure 11:
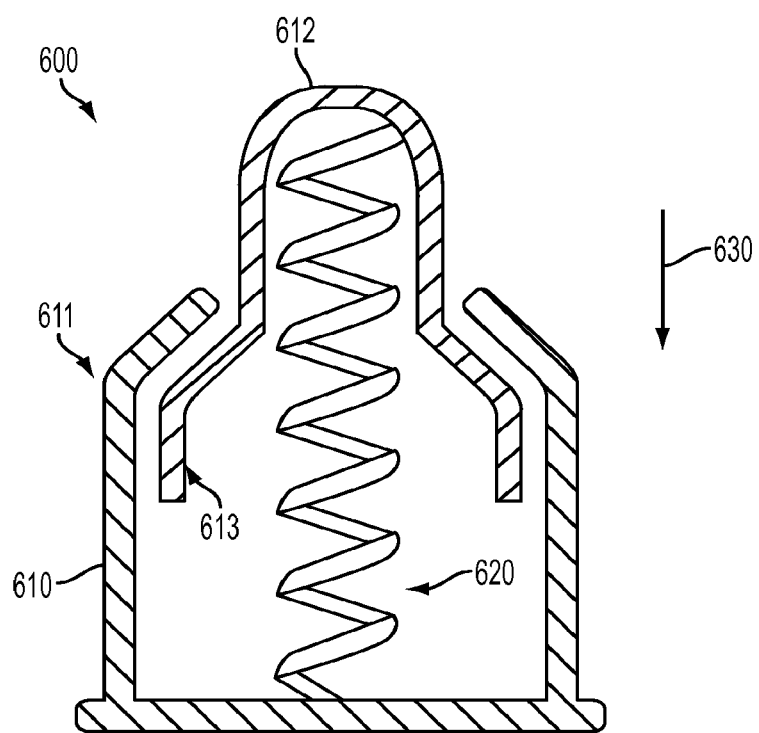
FIG. 11 shows a side cross-sectional view of a spring-loaded pin connector, according to an exemplary embodiment.

Pins used in the electrical connections of the exemplary embodiments described herein may be spring-loaded pins, according to an exemplary embodiment. Spring-loaded pins may be, for example, Pogo™ Pins of Everett Charles Technologies (ECT). Turning to FIG. 11, a side cross-sectional view is shown of a spring-loaded pin 600. Spring-loaded pin 600 includes a first portion 610, which may be electrically connected (e.g., via soldering or other method known to one of ordinary skill in the art) to a circuit board (not shown) or other component, and a second portion 612 configured to move relative to first portion 610. For example, spring-loaded pin 600 may include a spring 620 joining first portion 610 to second portion 612 so that when a force is applied along direction 630 to second portion 612, such as by a corresponding spring-loaded pin (not shown) engaging spring-loaded pin 600, spring 620 is compressed and second portion 612 may move relative to first portion 610 to accommodate engagement of spring-loaded pin 600 with the corresponding pin. First portion 610 and second portion 612 may remain in electrical contact via respective side portions 611 and 613 as second portion 612 moves relative to first portion 610. Thus, spring-loaded pins may permit axial variation in a distance between two connector ends, including a distance between respective circuit boards of the connector ends that the spring-loaded pins are respectively connected to. Thus, spring-loaded pins may accommodate higher compression forces when the distance is relatively small and may accommodate smaller compression forces when the distance is relatively large. According to an exemplary embodiment, first and second portions 610 and 612 may be made of an electrically conductive material and may be plated with a material, such as, for example, gold, to minimize or prevent oxidation.

As shown in the exemplary embodiments of FIGS. 9 and 10, connector ends 510 and 512 may respectively include second electrical connections 570 and 572. According to an exemplary embodiment, electrical connections 570 and 572 may include electrical connectors to form an electrical connection, such as, for example, respective arrays of pins 574 and 576 or other types of electrical connections. Pins of arrays 574 and 576 may be, for example, spring-loaded pins configured according to the exemplary embodiment of FIG. 11. Pin arrays 574 and 576 may each be, for example, an array of four pins, eight pins, or other numbers of pins, according to an exemplary embodiment.

Second electrical connections 570 and 572 may be used to transmit control signals (e.g., data signals) when connector ends 510 and 512 are fully connected with one another, such as according to the exemplary embodiment of FIGS. 6-8. According to an exemplary embodiment, control signals (e.g., high speed communication signals) may be sent along electrical connections 570 and 572 according to, for example, low-voltage differential signaling (LVDS). Because such control signals could emit or be affected by electrical noise, electrical connections 570 and 572 may respectively include shielding 571 and 573 to minimize or eliminate the noise, such as from electrical interference. According to an exemplary embodiment, the electrical shielding of the various exemplary embodiments described herein may also function to control impedance. For instance, to promote signal quality, the impedance of the electrical shielding should match, or be close to, the impedance of the connections of the connector ends.

First electrical connections 560 and 562 need not include shielding, such as when first electrical connections 560 and 562 are used to transmit electrical power, although first electrical connections 560 and 562 could include shielding when used for other applications, according to the exemplary embodiments described herein.

As shown in the end views of the exemplary embodiments of FIGS. 9 and 10, electrical shielding 571 and 573 may respectively surround the electrical connectors, such as pin arrays 574 and 576, of electrical connections 570 and 572. In view of this, electrical shielding 571 and 573 may each be a member having a substantially tubular shape so electrical shielding 571 and 573 may respectively surround the electrical connectors of electrical connections 570 and 572. For example, the electrical shielding 571, 573 may form a perimeter around the electrical connectors, such as pin arrays 574 and 576 of electrical connections 571 and 573. However, electrical shielding 571 and 573 are provided as separate components that engage with one another due to the ability of connector ends 510 and 512 to connect and disconnect from one another. For example, when connector ends 510 and 512 are connected to one another, electrical shielding 571 and 573 should contact with one another to minimize or eliminate noise in signals sent between electrical connections 570 and 572 even though electrical shielding 571 and 573 are separate pieces.

Figure 12:
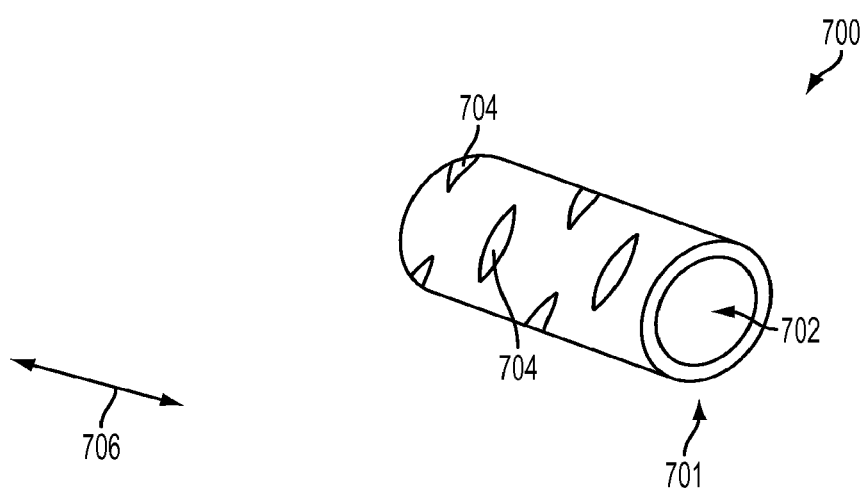
FIG. 12 shows a perspective view of a deformable electrical shielding member, according to an exemplary embodiment.

In view of these considerations, it may be desirable to form at least one of electrical shielding 571 and 573 to be a deformable member to facilitate positive engagement between electrical shielding 571 and 573. By forming at least one of electrical shielding 571 and 573 as a deformable member, the shielding may accommodate variations in the distance between connector ends 510 and 512 when the ends are joined together. Turning to FIG. 12, a perspective view of an exemplary embodiment of an electrical shielding member 700 is shown that is configured as a deformable member. Electrical shielding member 700 may include an end 701 with an aperture 702 through which electrical connectors, such as pin arrays 574 or 576 of electrical connections 570 or 572, may extend to join with electrical connectors of a corresponding electrical connection.

Figure 13:
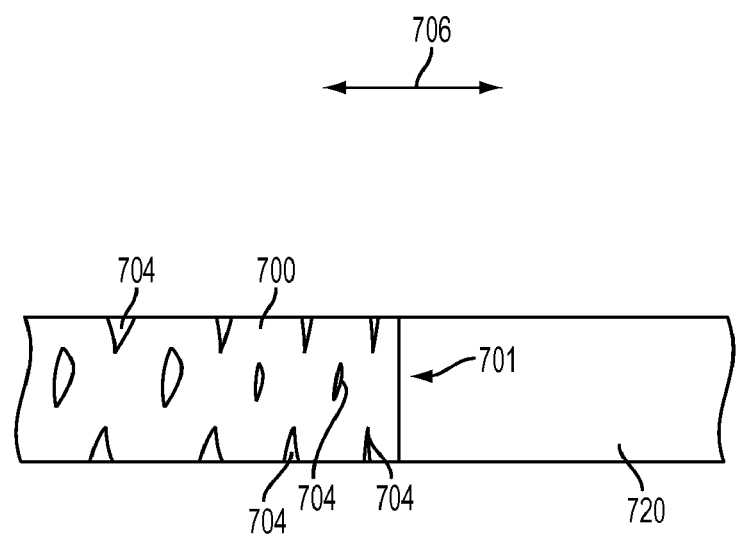
FIG. 13 shows a side view of the deformable electrical shielding member of FIG. 12 in engagement with another electrical shielding member.

According to an exemplary embodiment, electrical shielding member 700 may be deformable along axial directions 706, such as, for example, compressing along axial directions 706, when electrical shielding member 700 engages another electrical shielding member. To facilitate deformation of electrical shielding member 700 along directions 706, electrical shielding member 700 may include areas of material weakness, according to an exemplary embodiment. For example, electrical shielding member 700 may include gaps 704 where material of electrical shielding member 700 has been removed or is otherwise absent. Gaps 704 may facilitate compression of electrical shielding member 700 along axial directions 706. For example, FIG. 13 shows a side view of a second electrical shielding member 720 engaged with end 701 of deformable electrical shielding member 700 so that a compressive load is applied along axial directions 706. As a result, at least a portion of gaps 704 of electrical shielding member 700 compress and close at least partially, such as gaps 704 proximate to end 701, causing electrical shielding member 700 to deform along axial directions 706 and form a positive engagement with electrical shielding member 720. In various exemplary embodiments, gaps 704 that compress may close completely along axial directions 706, although complete closure of gaps 704 is not necessary for electrical shielding member 700 to function as electrical shielding for electrical connections that extend through electrical shielding member 700. Although only one of electrical shielding members 700 and 720 (or electrical shielding 571 and 573) need be a deformable member, as shown in FIG. 13, each of electrical shielding members 700 and 720 (and electrical shielding 571 and 573) may be deformable member according to the exemplary embodiments described herein.

Figure 14:
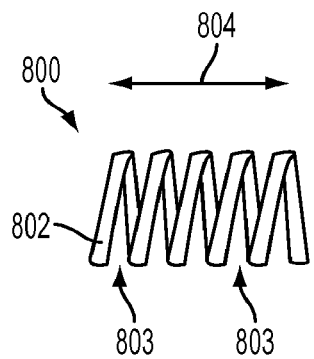
FIG. 14 shows a side view of a spring electrical shielding member, according to an exemplary embodiment.

Electrical shielding of the various exemplary embodiments described herein may be provided as a substantially tubular member, such as electrical shielding member 700 of the exemplary embodiment of FIG. 12, or electrical shielding may have other configurations. According to an exemplary embodiment, electrical shielding may be in the form of a spring, such as electrical shielding spring 800 shown in the exemplary embodiment of FIG. 14. When a compressive force is applied along axial directions 804, such as when spring 800 engages another electrical shielding member, windings 802 may be deformed so that gaps 803 between windings 802 of spring 800 decrease in size. Although the compressive force may cause windings 802 to press against one another so that gaps 803 are eliminated and spring 800 essentially becomes a substantially tubular member, the elimination of gaps 803 is not necessary for spring 800 to function as electrical shielding.

Figure 15:
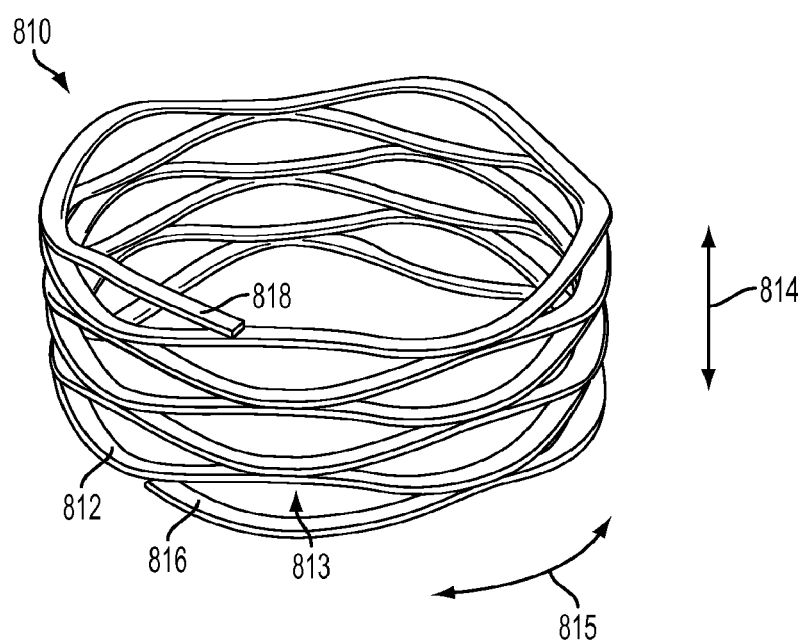
FIG. 15 shows an end view of a wave spring electrical shielding member, according to an exemplary embodiment.

According to an exemplary embodiment, electrical shielding may be in the form of a wave spring 810 with undulating windings 812, as shown in FIG. 15. When a compressive force is applied along axial directions 814, gaps 813 between windings 812 may decrease in size and may even be eliminated, although elimination of gaps 813 is not necessary for wave spring 810 to function as electrical shielding. Wave spring 810 may have an inner diameter ranging from, for example, about 0.300 inches to about 0.330 inches, an outer diameter ranging from, for example, about 0.350 inches to about 0.390 inches, a winding 812 thickness ranging from, for example, about 0.0075 inches to about 0.0105 inches, and an uncompressed length (i.e., free length) ranging from, for example, about 0.315 inches to about 0.330 inches. Wave spring 810 is not limited to these dimensions and may include other lengths, as may be desired in various applications. Wave spring 810 may be a multilayer wave spring with respect to axial directions 814, according to an exemplary embodiment. In a multilayer wave spring, windings 812 may extend along a circumferential direction to create a series of layers upon each other along axial directions 814, such as by extending between a first end 816 and a second end 818 of wave spring 810.

Electrical shielding of the various exemplary embodiments described herein may be made of a material to facilitate both insulation (shielding) for electrical connections and deformation. For instance, an electrical shielding material may have a low electrical resistance. According to an exemplary embodiment, the electrical shielding may be made of, for example, beryllium copper alloy or other metal or another alloy having a low electrical resistance. According to an exemplary embodiment, electrical shielding may be coated with an anti-oxidation material that also permits an electrical connection, such as, for example, gold. The electrical shielding may be electrically connected (e.g., via soldering or other electrical connection) to electronic components of connector ends, such as for, example, circuit boards of the connector ends. Connections with the electrical components may also be coated with an anti-oxidation material, such as, for example, gold.

Although the electrical shielding of the various exemplary embodiments above has been described in the context of connection interfaces within an arm of a patient side cart, such shielding may be used in other locations of the patient side cart. For example, the shielding may be used in an electrical connection between an instrument and an arm of a patient side cart, such as in an electrical connection between force transmission mechanism 162 and actuation interface assembly 152 of the exemplary embodiment of FIG. 1. Further, electrical shielding in accordance with various exemplary embodiments may be used in electrical connections not within a patient side cart, such as in electrical connections between two objects that can be disconnected and connected with one another.

Figure 16:
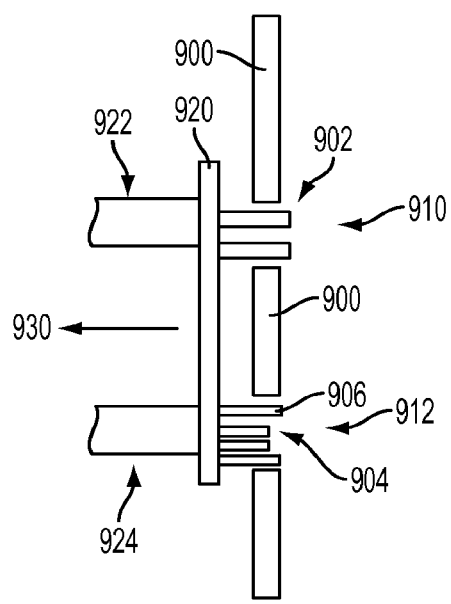
FIG. 16 shows a side cross-sectional view of an end of a component with electrical connections to a circuit board, according to an exemplary embodiment.

Electrical connections of the exemplary embodiments described herein may be connected to an electrical substrate, such as, for example, a circuit board. Turning to FIG. 16, a cross-sectional side view is shown of an end face 900 of a connector end of a component, such as connector end 510 of the exemplary embodiment of FIG. 9, with arrays of electrical connector pins 902 and 904 and electrical shielding 906 extending through end face 900 to provide electrical connections, similar to electrical connections 560 and 570 of the exemplary embodiment of FIG. 9. As shown in FIG. 16, pin arrays 902 and 904 and electrical shielding 906 may be connected to a circuit board 920, which in turn may be connected to electrical wires 922 and 924 or other types of electrical conduits/connections to supply electrical and/or control (data) signals transmitted via pin arrays 902 and 904. For instance, electrical energy and control (data) signal transmitted via pin arrays 902 and 904 and through electrical wires 922 and 924 may be used to actuate an instrument connected to an arm, such as instrument 160 of the exemplary embodiment of FIG. 1.

Because compressive forces may be applied to the pins of pin arrays 902 and 904 and to electrical shielding 906, circuit board 920 may be compliant to permit bending of circuit board 920, thereby accommodating some of the force applied to pins of arrays 902 and 904 and to electrical shielding 906. For example, when compressive forces 910 and 912 are applied to pin arrays 902 and 904 and to electrical shielding 906, circuit board 920 may be configured to be compliant and bend in direction 930 to accommodate a portion of the compressive forces 910 and 912, as shown in the exemplary embodiment of FIG. 16.

Figure 17:
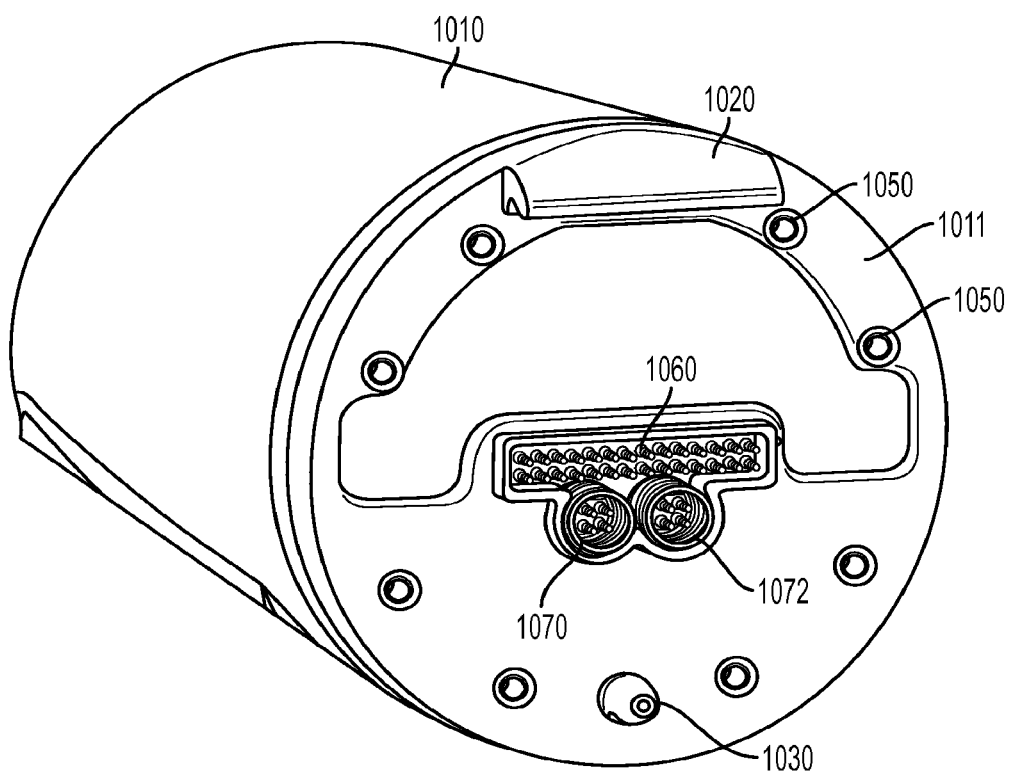
FIG. 17 shows a perspective end view of a first connector end, according to another exemplary embodiment.
Figure 18:
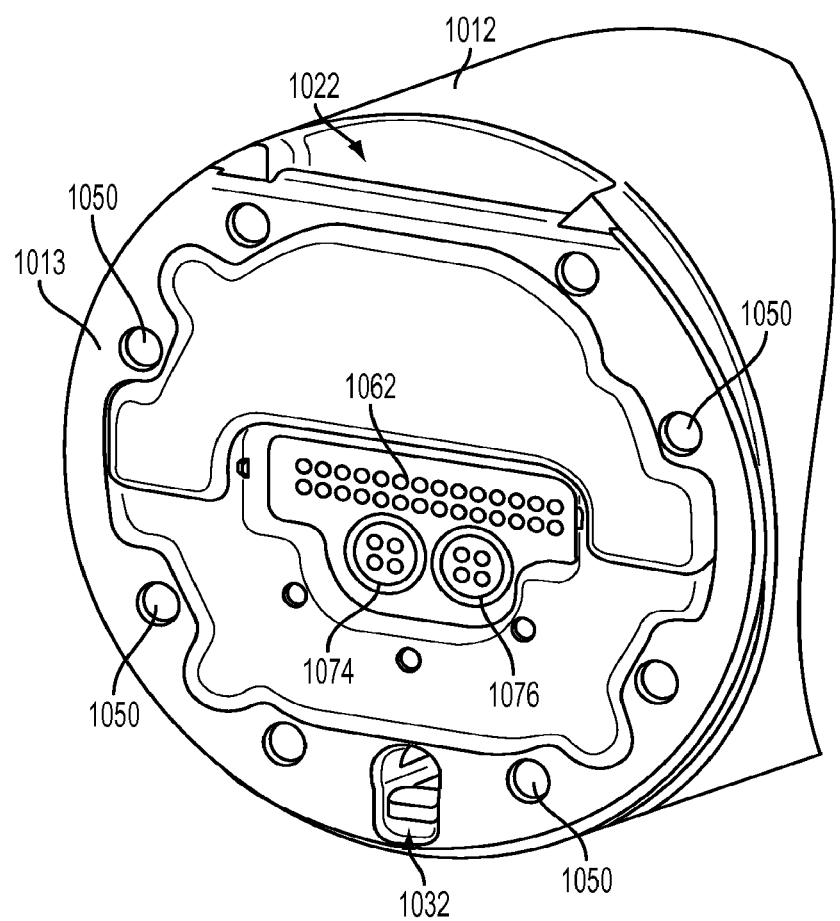
FIG. 18 shows a perspective end view of a second connector end, according to another exemplary embodiment.

The various exemplary embodiments described herein contemplate other arrangements than those described above. As shown in FIGS. 17 and 18, a first connector end 1010 and a second connector end 1012 may have other arrangements than those shown in FIGS. 5, 9, and 10. For example, first connector end 1010 may include a hook 1020, protrusion 1030, holes 1050 for fasteners, and an electrical connection 460 similar to corresponding features of first connector end 410 of the exemplary embodiment of FIG. 5. Similarly second connector end 1012 may include a slot 1022 to receive hook 1020, a recess 1032 to receive protrusion 1030, holes 1050 for fasteners, and an electrical connection 460 similar to corresponding features of second connector end 412 of the exemplary embodiment of FIG. 5. However, each of first and second connector ends 1010, 1012 include a plurality of electrical connections that are shielded according to the various exemplary embodiments described herein. For example, first connector end 1010 includes a first shielded electrical connection 1070 and a second shielded electrical connection 1072, while second connector end 1012 includes a first shielded electrical connection 1074 and a second shielded electrical connection 1076 to mate with shielded electrical connections 1070, 1072 of first connector end 1010. According to an exemplary embodiment, one set of complementary shielded electrical connections (e.g., shielded electrical connections 1070 and 1076) may be used to transmit signals and another set of complementary shielded electrical connections (e.g., shielded electrical connections 1072 and 1074) may be used to receive signals. According to another exemplary embodiment, the electrical connections for shielded electrical connections 1070 and 1072 may be provided as a single shielded electrical connection instead of separate shielded electrical connections. Similarly, the electrical connections for shielded electrical connections 1074 and 1076 may be provided as a single shielded electrical connection instead of separate shielded electrical connections.

Although first and second connector ends 1010, 1012 are depicted as including two shielded electrical connections, the connector ends of the various exemplary embodiments described herein are not limited to two shielded electrical connections but may instead include, for example, three, four, five, six or more shielded electrical connections.

According to an exemplary embodiment, the electrical connections of opposing connector ends may extend from respective faces of the connector ends by a substantially equal amount, as indicated in the exemplary embodiment of FIG. 5. However, the various exemplary embodiments described herein are not limited to such an arrangement and may include electrical connections that extend from connector end faces by differing amounts. For example, the electrical connections of one connector end may project from the face of a connector end while the electrical connections of a corresponding connector end are recessed into the face of the corresponding connector end. As shown in the exemplary embodiments of FIGS. 17 and 18, electrical connections 1060, 1070, 1072 may project from face 1011 of first connector end 1010 while electrical connections 1062, 1074, 1076 may be recessed into face 1013 of second connector end 1012. By making one connection project from a face of a connector end, electrical contact is facilitated between connections on opposing faces before the faces contact one another and prevent further movement of the faces.

Figure 19:
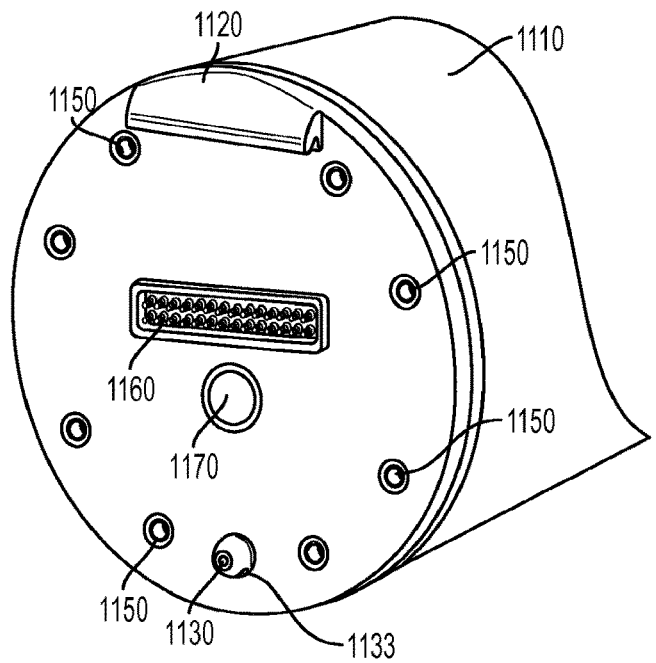
FIG. 19 shows a perspective end view of a first connector end, according to another exemplary embodiment.
Figure 20:
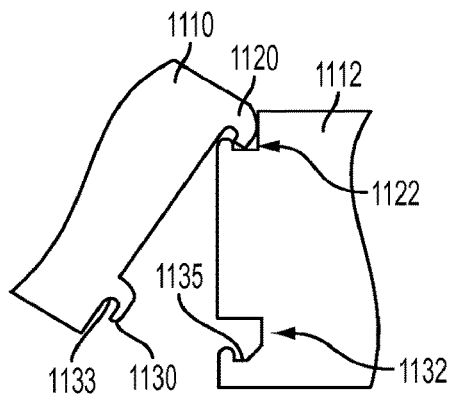
FIG. 20 shows a side view of an initial primary mechanical connection using the connector end of FIG. 19, according to an exemplary embodiment.
Figure 21:
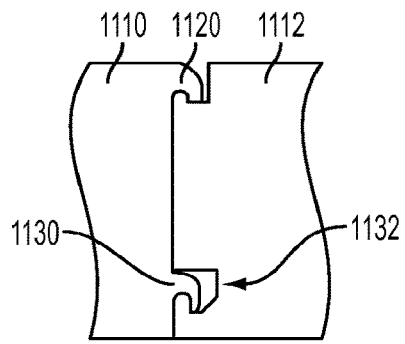
FIG. 21 shows the two connector ends of FIG. 20 in a fully connected state.

According to an exemplary embodiment, a protrusion to align connector ends, such as when the connector ends are joined to one another, may include a feature to fasten the connector ends to one another. Turning to FIG. 19, a first connector end 1110 is shown that includes a hook 1120, holes 1150 for fasteners, a first electrical connection feature 1160, and a second electrical connection feature 1170, each of which may be configured according to the various exemplary embodiments described herein. First connector end 1110 may further include a protrusion 1130 that is similar to protrusion 430 and 530 of the exemplary embodiments of FIGS. 5 and 9, except protrusion 1130 includes a fastening structure. For example, protrusion 1130 may include a latch structure 1133, as shown in the exemplary embodiment of FIG. 19. As shown in FIG. 20, first connector end 1110 may be initially connected with a second connector end 1112 having a slot 1122 receiving hook 1120 and a recess 1132 to receive protrusion 1130 (for example, similar to the exemplary embodiment of FIG. 6), with recess 1132 including a latch structure 1135 corresponding to latch structure 1133 of protrusion 1130. As shown in FIG. 21, which depicts first and second connector ends 1110 and 1112 in a fully connected state, recess 1132 may receive protrusion 1130, with latch structure 1135 of recess 1132 engaging latch structure 1133 of protrusion 1130 to provide a latch structure between first and second connector ends 1110 and 1112.

By utilizing the various connection interfaces of the exemplary embodiments described herein, a portion of an arm of a patient side cart may be removed to facilitate cleaning, repair, or replacement of the removable portion, with the removable portion being connected via a connection interface that permits replacement of both mechanical and electrical components at once rather than replacing mechanical and electrical units separately from one another. Further, disconnecting and connecting the removeable/replaceable portion is relatively easy, reliable, and can be done with minimal training and numerous times over the life cycle of the replaceable portion with minimal wear.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. An instrument support arm comprising:
   a first arm portion comprising a first connector end; and
   a second arm portion comprising a second connector end;
   wherein the second arm portion is removably connectable to the first arm portion via mating engagement of the first connector end and the second connector end;
   wherein the first connector end and the second connector end each comprise first complementary connection elements and second complementary connection elements;
   wherein the first complementary connection elements are engageable with each other to form a pivot coupling between the first arm portion and the second arm portion;
   wherein the first arm portion and the second arm portion are rotatable relative to each other about the pivot coupling;

wherein the second complementary connection elements each comprise electrical connection elements engageable to place the first and second arm portions in electrical communication;

wherein the second complementary connection elements are disengaged from each other in a first rotated position of the first arm portion and the second arm portion relative to each other about the pivot coupling;

wherein the second complementary connection elements are engaged with each other in a second rotated position of the first arm portion and the second arm portion relative to each other about the pivot coupling;

wherein the instrument support arm comprises electrical shielding at least partially surrounding the second complementary connection elements of the first connector end, the second complementary connection elements of the second connector end, or the second complementary connection elements of both the first connector end and the second connector end; and wherein the electrical shielding comprises a spring.

2. The instrument support arm of claim 1, wherein:
the spring is a wave spring.

3. The instrument support arm of claim 1, wherein:
the electrical shielding comprises a metal alloy.

4. The instrument support arm of claim 1, wherein:
the second complementary connection elements of the first arm portion comprise a first array of electrical contacts;
the second complementary connection elements of the second arm portion comprise a second array of electrical contacts; and
the first array of electrical contacts is positioned in contact with the second array of electrical contacts in the second rotated position of the first arm portion and the second arm portion relative to each other.

5. The instrument support arm of claim 1, wherein:
the second complementary connection elements of one or both of the first arm portion and the second arm portion comprise spring-loaded pins.

6. The instrument support arm of claim 1, wherein:
the second complementary connection elements of one or both of the first arm portion and the second arm portion comprise a corrosion-resistant material coating.

7. The instrument support arm of claim 1, wherein:
the first arm portion comprises a first planar face, and the second arm portion comprises a second planar face;
the second complementary connection elements of the first arm portion are on the first planar face, and the second complementary connection elements of the second arm portion are on the second planar face; and
the first and second planar faces are in a planar mating engagement with one another in the second rotated position of the first arm portion and the second arm portion relative to each other.

8. The instrument support arm of claim 1, wherein:
wherein the first complementary connection elements are disengagable from each other at the pivot coupling.

9. The instrument support arm of claim 1, wherein:
a first one of the first complementary connection elements comprises a hook; and
a second one of the first complementary connection elements comprises a slot configured to receive the hook.

10. The instrument support arm of claim 1, wherein:
each of the first arm portion and the second arm portion comprise complementary guide structures removably engageable with each other; and placement of the complementary guide structures into engagement aligns the second complementary connection elements for engagement in the second rotated position of the first arm portion and the second arm portion relative to each other.

11. The instrument support arm of claim 10, wherein:
a first one of the complementary guide structures is a female feature; and
a second of the complementary guide structures is a male feature configured to be received by the female feature.

12. The instrument support arm of claim 11, wherein:
the male feature comprises a free end rounded such that free end is received in the female feature as the first arm portion and the second arm portion pivot relative to each other about the pivot coupling.

13. The instrument support arm of claim 10, wherein:
in a third rotated position of the first arm portion and the second arm portion relative to each other about the pivot coupling, the complementary guide structures are partially engaged with each other, and the second complementary connection elements are disengaged from each other; and
in a fourth rotated position of the first arm portion and the second arm portion relative to each other about the pivot coupling, the complementary guide structures are engaged with each other, and the second complementary connection elements are engaged with each other.

14. The instrument support arm of claim 1, wherein:
the first arm portion or the second arm portion is configured to be coupled to a main boom of a patient side cart of a teleoperated manipulator system.

15. The instrument support arm of claim 14, wherein:
one of the first arm portion and the second arm portion is a positioning portion configured to be articulated to a desired position relative to the main boom and locked in the desired position.

16. The instrument support arm of claim 15, wherein:
the other of the first arm portion and the second arm portion is a manipulator portion comprising one or more joints configured to be actively articulated based on commands received at a surgeon console of the teleoperated manipulator system.

17. An instrument support arm, comprising:
a first arm portion comprising a first connector end; and
a second arm portion comprising a second connector end;
wherein the second arm portion is removably connectable to the first arm portion via mating engagement of the first connector end and the second connector end;
wherein the first connector end and the second connector end each comprise first complementary connection elements and second complementary connection elements;
wherein the first complementary connection elements are engageable with each other to form a pivot coupling between the first arm portion and the second arm portion;
wherein the first arm portion and the second arm portion are rotatable relative to each other about the pivot coupling;
wherein the second complementary connection elements comprise electrical connection elements engageable to place the first and second arm portions in electrical communication;
wherein the second complementary connection elements are disengaged from each other in a first rotated position of the first arm portion and the second arm portion relative to each other about the pivot coupling;

wherein the second complementary connection elements are engaged with each other in a second rotated position of the first arm portion and the second arm portion relative to each other about the pivot coupling;

wherein the instrument support arm comprises electrical shielding at least partially surrounding the electrical connection element of the first connector end, the electrical connection element of the second connector end, or the electrical connection elements of both the first connector end and the second connector end;

wherein the electrical shielding comprises a spring;

wherein the spring is in an uncompressed state in the first rotated position of the first arm portion and the second arm portion relative to each other; and wherein the spring is in a compressed state in the second rotated position of the first arm portion and the second arm portion relative to each other.

18. The instrument support arm of claim 17, wherein:
the spring comprises a wave spring.

19. The instrument support arm of claim 17, wherein:
the second complementary connection elements of the first arm portion comprise a first array of electrical contacts;

the second complementary connection elements of the second arm portion comprise a second array of electrical contacts; and the first array of electrical contacts is positioned in contact with the second array of electrical contacts in the second rotated position of the first arm portion and the second arm portion relative to each other.

20. An instrument support arm comprising:
a first arm portion comprising a first connector end; and
a second arm portion comprising a second connector end;
wherein the second arm portion is removably connectable to the first arm portion via mating engagement of the first connector end and the second connector end;

wherein the first connector end and the second connector end each comprise first complementary connection elements and second complementary connection elements;

wherein the first complementary connection elements are engageable with each other to form a pivot coupling between the first arm portion and the second arm portion;

wherein the first arm portion and the second arm portion are rotatable relative to each other about the pivot coupling;

wherein the second complementary connection elements comprise electrical connection elements engageable to place the first and second arm portions in electrical communication;

wherein the second complementary connection elements are disengaged from each other in a first rotated position of the first arm portion and the second arm portion relative to each other about the pivot coupling;

wherein the second complementary connection elements are engaged with each other in a second rotated position of the first arm portion and the second arm portion relative to each other about the pivot coupling;

each of the first arm portion and the second arm portion comprise complementary guide structures removably engageable with each other;

placement of the complementary guide structures into engagement aligns the second complementary connection elements for engagement in the second rotated position of the first arm portion and the second arm portion relative to each other; and the second complementary connection elements are located between the first complementary connection elements and the complementary guide structures along a radial direction of the instrument support arm in the second rotated position of the first arm portion and the second arm portion relative to each other.

21. The instrument support arm of claim 20, wherein:
in a third rotated position of the first arm portion and the second arm portion relative to each other about the pivot coupling, the complementary guide structures are partially engaged with each other, and the second complementary connection elements are disengaged from each other; and in a fourth rotated position of the first arm portion and the second arm portion relative to each other about the pivot coupling, the complementary guide structures are engaged with each other, and the second complementary connection elements are engaged with each other.

22. The instrument support arm of claim 20, wherein:
the first arm portion or the second arm portion is configured to be coupled to a main boom of a patient side cart of teleoperated manipulator system.

* * * * *